US00PP18722P2

(12) United States Plant Patent
Utecht

(10) Patent No.: US PP18,722 P2
(45) Date of Patent: Apr. 8, 2008

(54) ***PELARGONIUM* PLANT NAMED 'FISROPINK'**

(50) Latin Name: *Pelargonium ×hortorum*
Varietal Denomination: Fisropink

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 11/505,613

(22) Filed: Aug. 17, 2006

(51) Int. Cl.
*A01H 5/00* (2006.01)

(52) U.S. Cl. ..... Plt./328
(58) Field of Classification Search ..... Plt./328, Plt./329, 324
See application file for complete search history.

(56) References Cited
PUBLICATIONS
UPOV–ROM GTITM, Plant Variety Database, Jan. 2007, GTI Jouve Retrieval Software, Citation for Pelargonium 'Fisroponk 'and 'Fit 462 ', 2 pages.*
Flora–Nova Pflanzen GmbH [online ][retrieved on Jul. 24, 2007]. Retrieved from the Internet:<http://www.top500.de/details/475/flora–nova_pflanzen_gmbh_germany.php>2 pages.*
* cited by examiner

*Primary Examiner*—Kent Bell
*Assistant Examiner*—June Hwu
(74) *Attorney, Agent, or Firm*—Jondle & Associates, P.C.

(57) ABSTRACT

A new cultivar of *pelargonium* particularly characterized by having cup-shaped, brilliant-pink, semi-double flowers with white eyes, floriferous with large inflorescences on long peduncles, medium-green and large foliage with distinct zonation, a tall plant habit with vigorous growth, a rounded and moderately tight plant habit and a continuous and mid-season flowering response, is disclosed.

1 Drawing Sheet

Genus and species: *Pelargonium×hortorum.*
Variety denomination: 'Fisropink'.

BACKGROUND OF THE NEW PLANT

The present invention comprises a new and distinct cultivar of *pelargonium*, botanically known as *Pelargonium× hortorum,* and hereinafter referred to by the cultivar name 'Fisropink'. The new cultivar is a product of a planned breeding program which had the objective of creating new varieties having pink flowers, a good stability of flower color, medium-green foliage and vigorous growth. 'Fisropink' was discovered as a seedling resulting from the cross of the female parent 'Fisblu' (U.S. Plant Pat. No. 9,764), having mainly pink semi-double flowers with purple and white markings, and the male parent 'Dresdner Puppe Rosa mit Auge' (Plant Breeder's Rights protection in Europe under 'Drepenosa') having pink flowers with deep-pink eyes.

The new cultivar was created in 1999 in Hillscheid, Germany and has been asexually reproduced repeatedly by vegetative cuttings in Galdar, Gran Canaria, Spain, and Hillscheid, Germany over a five-year period. It has been found to retain its distinctive characteristics through successive asexual propagations. 'Fisropink' reproduces true to type in successive generations of asexual reproduction.

Plants Breeder's Rights for this cultivar were applied for in Germany on Apr. 4, 2005 and Canada on Apr. 20, 2005.

SUMMARY OF THE INVENTION

The following are the most outstanding and distinguishing characteristics of this new cultivar when grown under normal horticultural practices in Hillscheid, Germany.

1. Cup-shaped, brilliant-pink, semi-double flowers with white eyes;

2. Floriferous with large inflorescences on long peduncles;
3. Medium-green and large foliage with distinct zonation;
4. A tall plant habit with vigorous growth;
5. A rounded and moderately tight plant habit; and
6. A mid-season and continuous flowering response.

DESCRIPTION OF THE PHOTOGRAPH

This new *pelargonium* plant is illustrated by the accompanying photograph which shows overall plant habit including inflorescences, buds, and foliage of the plant; the colors shown are as true as can be reasonably obtained by conventional photographic procedures. The photograph is of a 12- to 14-week-old, un-pinched plant grown from rooted cuttings, in 14-cm pot and grown under greenhouse and outdoor conditions which approximate those generally used in commercial practice.

DESCRIPTION OF THE NEW CULTIVAR

The following detailed description sets forth the distinctive characteristics of 'Fisropink'. The data which define these characteristics were collected from asexual reproductions carried out in Hillscheid, Germany. The plant history was taken on 11-week-old, un-pinched plants in 12-cm pots in a greenhouse during late May 2005. Color readings were taken under natural light in late May from flowers grown in the greenhouse. Color references are primarily to the RHS Colour Chart of The Royal Horticultural Society of London (RHS) (2001).

DETAILED BOTANICAL DESCRIPTION

Classification:

*Family.*—Geraniaceae.

*Botanical.*—*Pelargonium×hortorum.*

*Common name.*—Zonal geranium.

Parentage:

*Female parent.*—'Fisblu' a proprietary *pelargonium* plant having mainly pink semi-double flowers with purple and white markings (U.S. Plant Pat. No. 9,764).

*Male parent.*—'Dresdner Puppe Rosa mit Auge' a *pelargonium* plant having pink flowers with deep-pink eyes (Plant Breeder's Rights protection in Europe under 'Drepenosa').

Plant:

*Form.*—Shrub, self-branching, rounded shape.

*Branching habit.*—6 to 7 branches per plant.

*Height* (*measured from base of the stem to the tips of the branches, excluding the inflorescence, 11 weeks old*).—21.7 cm.

*Width* (*plant diameter at 11-weeks-old*).—36.3 cm.

*Time to produce a flowering plant.*—Plants had an average of 0.5 opened inflorescences about 8 weeks after planting rooted cuttings in Hillscheid, Germany.

*Outdoor plant performance.*—Plants continuously flower; a count in late May of 2005 in Hillscheid, Germany produced about 4.5 inflorescences per plant; in late summer produced about 15 to 20 umbels per plant (26-weeks-old).

Leaves:

*Arrangement.*—Alternate, at flowering stems opposite.

*Immature leaf color.*—Medium green. Upper surface: RHS 137C. Lower surface: RHS 137D.

*Mature leaf color.*—Upper surface: RHS 137B (medium-green). Lower surface: RHS 137D.

*Zonation color.*—RHS 166A (brown) with a medium distinctness.

*Zonation diameter.*—Inner diameter of ring: 5.6 cm. Band or belt of zonation: 1.0 cm to 1.5 cm.

*Size.*—Length: 7.0 cm. Width: 12.1 cm.

*Shape.*—Relatively large, kidney-shaped with weak lobes and an open gap between lowest lobes.

*Apex.*—Rounded.

*Base.*—Cordate.

*Margin.*—Bi-crenate, somewhat wavy.

*Texture.*—Upper surface is smooth, dull, and velvety.

*Petioles.*—Color: RHS 143C (light-green). Length: 7.0 cm to 12.0 cm. Diameter: 0.3 cm. Texture: Covered with fine pubescence.

Stems:

*Stem color.*—RHS 143C.

*Length.*—13 cm to 19 cm.

*Diameter.*—0.7 to 0.8 cm.

*Internode length.*—1.0 cm to 2.5 cm.

*Texture.*—Appear smooth, yet covered with very short pubescence.

Inflorescence bud: (just before petals unfold)

*Shape.*—Elliptical.

*Size.*—Length: 1.4 cm to 1.6 cm. Width: 0.7 cm to 0.8 cm.

*Color of sepals.*—RHS 143C (light-green).

*Color of petals.*—RHS 55A.

Inflorescence:

*Inflorescence type.*—An umbel composed of 20 to 30 flowers

*Umbel.*—Shape: Nearly semi-spherical Diameter: 12.1 cm Height (depth): 5.5 cm.

*Lastingness of umbel on the plant.*—About 16 days.

*Peduncles.*—Color: RHS 143C (light-green). Length: 24.6 cm. Diameter: 0.5 cm. Texture: With dense, short glandular hair.

*Pedicel.*—Color: Mainly RHS 143C (light-green) with RHS 181B (reddish-brown) anthocyanin in parts. Length: 3.2 cm. Diameter: 0.15 cm. Texture: Very short glandular hairs.

Corolla:

*Shape of corolla.*—Round outline with both the upper petals and lower petals roughly the same size and cup-shaped.

*Form.*—Semi-double.

*Diameter.*—5.2 cm.

*Depth.*—1.0 cm to 1.5 cm.

*Number of petals.*—6 to 7.

*Petaloids.*—Number: 1 to 2. Shape: Variable, shorter and narrower than the petals, often folded or twisted. Color: RHS 58C (pink) or RHS 69C (pale-pink).

*Lastingness of individual flowers on plant.*—8 days at 18° C.

*Fragrance.*—None.

Petals:

*Shape.*—Obovate.

*Apex.*—Rounded.

*Base.*—Acute.

*Margin.*—Entire.

*Texture.*—Smooth, slightly glossy.

*Upper petals.*—Length: 2.3 cm to 2.5 cm. Width: 1.8 cm to 2.0 cm. Color: Upper surface: Between RHS 58B and RHS 58C. Lower surface: RHS 68B near the margin and deeper pink, with RHS 58C veins at the base of the petal. Markings: Distinct RHS 155D (white) bases (⅓ or more of the length) and very fine RHS 68B (pink) veins.

Lower petals.—Length: 2.4 cm to 2.6 cm. Width: 2.2 cm to 2.3 cm. Color: Upper surface: RHS 58C. Lower surface: Between RHS 68B and RHS 68C. Markings: Absent.

Sepals:

*Number.*—5.

*Color.*—Upper (inner) surface: RHS 143B (light-green). Lower (outer) surface: RHS 143C.

*Length.*—1.0 cm to 1.1 cm.

*Width.*—Largest upper sepal: 0.3 cm to 0.4 cm. Other sepals: 0.2 cm to 0.3 cm.

*Shape.*—Lanceolate.

*Apex.*—Acute.

*Base.*—Truncate.

*Margin.*—Entire.

*Texture.*—Dense glandular hair and sparse pubescence.

Reproductive organs:

*Androecium.*—Number of anthers: Usually 5. Filament length: 0.7 cm to 0.8 cm. Filament color: RHS 155D (white) to RHS 58C (reddish) at upper ends. Pollen color: RHS 28B (orange). Pollen amount: Moderate.

*Gynoecium.*—Pistil: Number: 1. Length: 0.8 cm. Stigma color: RHS N57B (red-purple). Stigma shape: 5 to 6 lobed. Style color: RHS N57B to RHS N57C. Style length: 0.3 cm. Style shape: Filiform (filament-like) with the lobes of the stigma at right angles.

Fruit and seed set: No seed set observed.

Disease and insect resistance: No particular resistance or susceptibility has been observed.

COMPARISON WITH PARENTAL AND COMMERCIAL CULTIVARS

'Fisropink' differs from the female parent 'Fisblu' (U.S. Plant Pat. No. 9,764) by having a more vigorous growth habit and foliage with distinct zonation, while the foliage of 'Fisblu' has nearly no zonation. In addition, the flowers of 'Fisropink' have distinct white bases and fine pink veins, while the flowers of 'Fisblu' have purple and white markings.

'Fisropink' differs from the male parent and commercial variety 'Dresdner Puppe Rosa mit Auge' (Plant Breeder's Rights protection in Europe under 'Drepenosa') in that 'Dresdner Puppe Rosa mit Auge' has pink markings on the petals, while 'Fisropnk' does not have pink markings. In addition, 'Fisropink' has 6 to 7 petals, semi-double flowers, has a tall plant habit with vigorous growth, while Dresdner Puppe Rosa mit Auge has 5 petals, single to weakly semi-double flowers and a compact to medium-sized plant habit.

'Fisropink'differs from the commercial variety 'Fisblufort' (U.S. Plant Pat. No. 13,195) by having larger leaves and a more vigorous growth habit than 'Fisblufort'. In addition, 'Fisropink'has brilliant pink flowers with white eyes, while 'Fisblufort' has bright pink flowers with red eyes.

'Fisropink'differs from the commercial variety 'Americana Pink III/Amri Pinka Three' (unpatented) by having lighter pink flowers with larger white eyes than 'Americana Pink III/Amri Pinka Three'. In addition, 'Fisropink' has foliage with distinct zonation, while 'Americana Pink III/Amri Pinka Three' has no zonation.

I claim:

1. A new and distinct cultivar of *pelargonium* plant as shown and described herein.

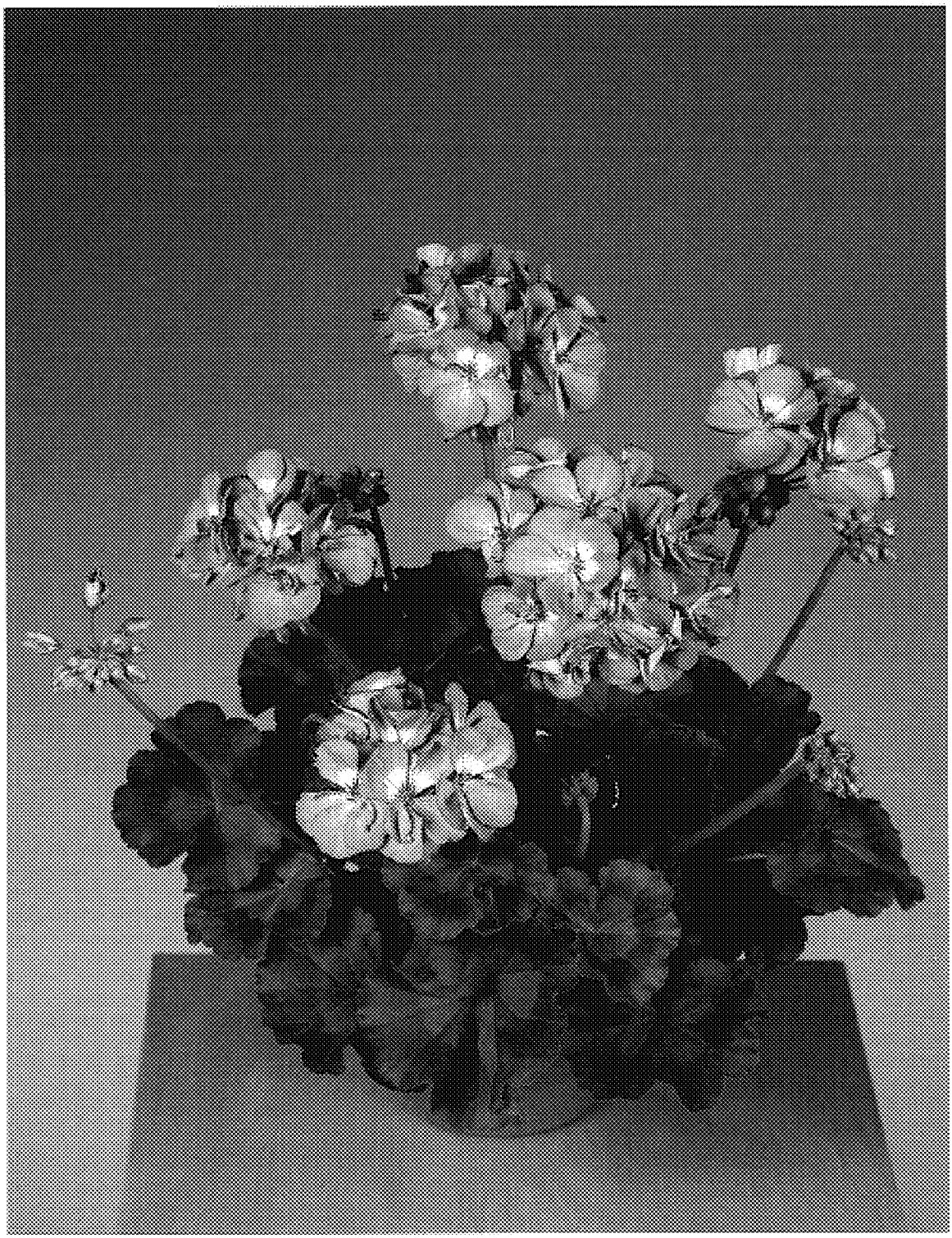

* * * * *